(12) United States Patent
Sumanaweera et al.

(10) Patent No.: US 6,482,161 B1
(45) Date of Patent: Nov. 19, 2002

(54) MEDICAL DIAGNOSTIC ULTRASOUND SYSTEM AND METHOD FOR VESSEL STRUCTURE ANALYSIS

(75) Inventors: Thilaka Sumanaweera, San Jose; Linyong Pang, Stanford, both of CA (US)

(73) Assignee: Acuson Corporation, Mountain View, CA (US)

( * ) Notice: Subject to any disclaimer, the term of this patent is extended or adjusted under 35 U.S.C. 154(b) by 19 days.

(21) Appl. No.: 09/607,020

(22) Filed: Jun. 29, 2000

(51) Int. Cl.$^7$ ................................................. A61B 8/00
(52) U.S. Cl. ...................................................... 600/454
(58) Field of Search .......................... 600/454, 36, 465, 600/437, 453, 476, 456, 485, 455, 441, 322, 439, 587

(56) References Cited

U.S. PATENT DOCUMENTS

| | | | |
|---|---|---|---|
| 5,365,929 A | * 11/1994 | Peterson | ...................... 600/456 |
| 5,474,073 A | 12/1995 | Schwartz et al. | |
| 5,623,930 A | 4/1997 | Wright et al. | |
| 5,771,896 A | 6/1998 | Sliwa, Jr. et al. | |
| 5,876,345 A | 3/1999 | Eaton et al. | |
| 5,928,151 A | 7/1999 | Hossack et al. | |
| 5,967,987 A | 10/1999 | Sumanaweera et al. | |
| 6,006,128 A | * 12/1999 | Izatt et al. | ................... 600/476 |
| 6,014,473 A | 1/2000 | Hossack et al. | |
| 6,045,508 A | 4/2000 | Hossack et al. | |
| 6,176,832 B1 | * 1/2001 | Habu et al. | ................... 600/485 |

OTHER PUBLICATIONS

Paik et al., "Automated Flight Path Planning for Virtual Ends" Medical Physics, May, 1998; 25(5): 629–637.

Scott Unbaugh, "Computer Vision and Image Processing—A Practical Approach . . . " Prentice Hall PTR, Upper Saddle River, NJ 07458.

Carlo Palombo, MD.; Ultrafast Three-Dimensional Ultrasound Application to Carotid Artery Imaging; 1998; pp. 1631–1637.

* cited by examiner

*Primary Examiner*—Marvin M. Lateef
*Assistant Examiner*—Ruby Jain

(57) ABSTRACT

Medical diagnostic ultrasound methods and systems for automated structure analysis are provided. Where the vessel bifurcates, such as the carotid artery, the common portion (i.e. the bifurcation bulb) is divided between the branches. For example, the common portion is divided as a function of a ratio of (1) the integral of ultrasound flow data at a cross-section of a first branch to (2) the integral of ultrasound flow data at a cross-section of a second branch. As another example, the intersection of three-dimensional surfaces perpendicular to the center axis of each branch within the common area divides the common portion. The ultrasound data representing the common portion is associated with each branch as a function of the division. This association assists with flow and structural analysis. For use with the bifurcation division discussed above or for other vessels, a method and system for automatically assigning a center (i.e. medial) axis of the vessel is provided. A center of flow for the vessel is determined, such as by: (1) calculating gradient values from ultrasound data representing flow in the vessel, (2) determining a magnitude of the gradient values for each spatial location, and (3) reducing a boundary of the vessel by an amount that is a function of the magnitude until a center of flow (i.e. line) is identified. The center of flow is assigned as the center of the axis. The determined center axis is used to identify constrictions or analyze flow for medical diagnosis. A memory and processor is provided for automatically performing the acts discussed above. Minimal user input allows the ultrasound system to automatically provide information assisting medical diagnosis.

35 Claims, 2 Drawing Sheets

MEDICAL DIAGNOSTIC ULTRASOUND SYSTEM AND METHOD FOR VESSEL STRUCTURE ANALYSIS

BACKGROUND

This invention relates to a medical diagnostic ultrasound system and method for vessel structure analysis.

Accurate diagnosis of constrictions in vessels, such as the carotid artery, assists medical treatment. Two or three-dimensional ultrasound images of the carotid are rendered from blood flow information. The user subjectively examines the geometry of the rendering for any constriction. This examination typically requires skill and experience to distinguish an actual stenosis from an image artifact or other natural vessel variations.

BRIEF SUMMARY

The present invention is defined by the following claims, and nothing in this section should be taken as a limitation on those claims. By way of introduction, the preferred embodiment described below includes a method and system for automated vessel structure analysis. Where the vessel bifurcates, such as the carotid artery, the common portion (i.e. the bifurcation bulb) is divided between the branches. For example, the common portion is divided as a function of a ratio of (1) the integral of ultrasound flow data at a cross-section of a first branch to (2) the integral of ultrasound flow data at a cross-section of a second branch. As another example, the intersection of planes perpendicular to the center axis of each branch within the common area divides the common portion. The ultrasound data representing the common portion is associated with each branch as a function of the division. This association assists with flow and structural analysis.

For use with the bifurcation division discussed above or for other vessels, a method and system for automatically assigning a center (i.e. medial) axis of the vessel is provided. A center of flow for the vessel is determined, such as by: (1) calculating gradient values from ultrasound data representing flow in the vessel, (2) determining a magnitude of the gradient values for each spatial location, and (3) reducing a boundary of the vessel by an amount that is a function of the magnitude of the ultrasound data until a center of flow (i.e. line) is identified. The center of flow is assigned as the center of the axis. The determined center axis is used to identify constrictions or analyze flow for medical diagnosis.

A memory and processor is provided for automatically performing the acts discussed above. Minimal user input allows the ultrasound system to automatically provide information assisting medical diagnosis.

Further aspects and advantages of the invention are discussed below in conjunction with the preferred embodiments.

DETAILED DESCRIPTION OF THE PREFERRED EMBODIMENTS

The center or medial axis of a vessel is automatically determined with an ultrasound system. Gradient values are determined in multiple dimensions for a plurality of spatial locations in a vessel by a processor. The magnitude of the gradient values is determined for each of the spatial locations. The boundary of the vessel is iteratively reduced by an amount that is a function of the magnitude of the ultrasound data. As a result of iterative reduction, a center of flow is located as a line associated with the last remaining spatial location for each cross-section of the vessel. The center axis of the vessel is assigned as the center of flow by the processor.

Using the above described identification of the center axis or other techniques, the common portion of a vessel bifurcation is divided between each branch. In one embodiment, the common portion is divided as a function of a ratio of an integral of ultrasound flow data at a cross-section of a first branch to an integral of ultrasound flow data at a cross-section of a second branch. The cross-sections in the first and second branches are selected as perpendicular to the center axis. At a cross-section within the common portion or for the volume of the common portion, data is attributed to each branch in correspondence with the ratio. In another embodiment, an intersection of planes that are each perpendicular to a center axis of one of at least two branches in the common portion defines the division between each branch.

I. System

Various ultrasound systems are capable of automatically determining a center axis or dividing a common portion of a bifurcated vessel. For example, a Sequoia®, Aspen™ or 128XP®ultrasound system manufactured by Acuson Corporation may be used. Other ultrasound systems, such as systems provided by other manufacturers as remote workstations, may be used.

Figure 1:
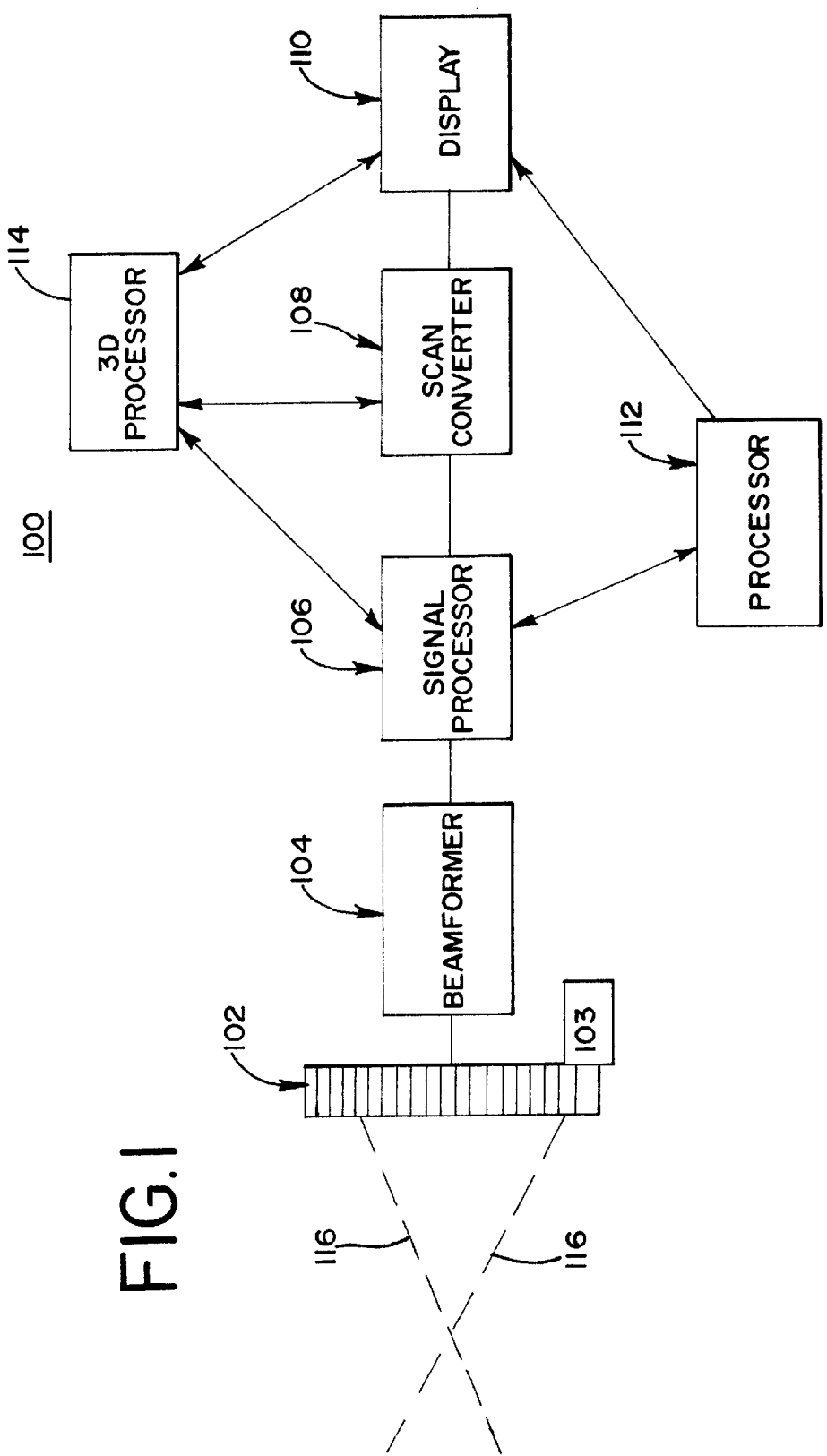
FIG. 1 is a block diagram of one embodiment of a medical diagnostic ultrasound system for automatically assisting with medical diagnosis.

FIG. 1 shows one embodiment of an ultrasound system for assisting medical diagnosis at 100. The system 100 includes a data path comprising a transducer 102, a beamformer 104, a signal processor (estimator) 106, a scan converter 108 and a display device 110. A processor 112 connects to the data path, such as connecting at least to the signal processor 106. A three-dimensional image processor 114 also connects to the data path, such as connecting with one or more of the signal processor 106, the scan converter 108 and the display device 110. In alternative embodiments, the three-dimensional image processor 114 is within the data path, such as being part of the signal processor 106 or scan converter 108, between the signal processor 106 and scan converter 108, or between the scan converter 108 and the display device 110.

The transducer 102 is any of various transducers, such as a linear or curved linear array of piezoelectric elements. In one embodiment, a multi-dimensional transducer is used. For example, multiple image registration or 1.5 or 2 dimensional transducers are used. These transducers include elements arrayed substantially on a plane (i.e. arrayed in two dimensions). For a description of multiple image registration transducers, see U.S. Pat. No. 6,014,473, the disclosure of which is incorporated herein by reference. One multiple image registration transducer embodiment includes elements in a plane arrayed in an I pattern. Three scan planes associated with the I pattern may be generated. For T or + beam pattern transducers, two scan planes associated with the T and + patterns, respectively, may be generated. Transducers with other element patterns may be used. For 1.5 or 2 dimensional transducers, any of the various scan plane formats or patterns may be generated.

In one embodiment, the transducer 102 is connected with a catheter or endoscope for insertion into a patient. For example, the transducer 102 is provided on an AcuNav™ Acuson ultrasound imaging catheter or the catheter described in U.S. Pat. No. 5,876,345, the disclosure of which is incorporated herein by reference. Other catheter and transducer devices may be used. As another example, the transducer 102 is provided on one of the endoscopes described in U.S. Pat. Nos. 5,771,896 or 6,045,508, (application Ser. No. 08/807,384, filed Feb. 27, 1998), the disclosures of which are incorporated herein by reference. Other endoscope and transducer devices may be used. In alternative embodiments, the transducer 102 comprises a hand held or mounted transducer for use external to the patient.

The beamformer 104 is constructed as known in the art. The beamformer 104 may comprise separate transmit and receive beamformers. The beamformer 104 produces excitation signals for each or a subset (i.e. a sub-aperture) of the elements of the transducer 102. The excitation signals are processed, such as by applying a relative delay and/or amplitude, to focus ultrasonic waveforms along one or more scan lines 116. The scan lines 116 may be at any of various angles relative to the transducer 102 and originate at various locations along the transducer 102. The plane defined by two or more scan lines or any linear combination of transducer elements comprises a scan plane.

The acoustic waveforms are reflected off of structures within a body, including moving fluid or contrast agents within an enclosed structure, as echoes. The echoes are detected by the elements of transducer 102 and provided as voltage signals to the beamformer 104. The beamformer 104 sums the voltage signals and outputs ultrasound data representative of structures along the one or more scan lines.

In one embodiment, the beamformer 104 includes a filter for isolating information in a desired frequency band. For example, a bandpass filter, a highpass filter, a lowpass or combinations thereof selectively pass one or both of data at the transmit fundamental frequency band or data at a harmonic of the fundamental frequency band. As another example, a demodulator and a filter are provided to isolate information at a desired frequency band.

The signal processor (estimator) 106 comprises a construction known in the art, such as a Doppler digital signal processor or filtering device for providing Doppler estimates from the representative ultrasound data. The signal processor 106 may also include a parallel B-mode processor or spectral Doppler processor. A clutter filter may also be included. The signal processor 106 estimates the Doppler velocity, energy, and/or variance for each of various points or ranges along each scan line. The estimates and any B-mode information may be stored in a memory, such as a CINE™ or image video loop memory.

The estimates, such as Doppler velocity, and/or any B-mode information representing areas in the scan plane or along a scan line are provided to the scan converter 108. The scan converter 108 is a processor or dedicated hardware for formatting the estimates into a Cartesian coordinate system for display.

The display device 110 comprises a monitor, such as a color monitor, flat panel display, television or other device for displaying an image. For two-dimensional imaging, the scan converted ultrasound data representing the scan plane is displayed on the display device 110 as a B-mode intensity, Doppler velocity, Doppler energy, or Doppler variance image. Images that are a combination of two or more of these types of data may also be generated.

The processor 112 is a digital signal processor or multi-purpose processor for associating or for identifying the center axis of a vessel and dividing common portions of a bifurcated vessel. Alternatively, other hardware, such as an accumulator, summer and buffer, may be used. The processor 112 obtains information, such as Doppler velocities, Doppler energies, Doppler variances, Doppler spectrum parameters, orientation information corresponding to the various scan lines and/or other information for identifying the center axis or dividing the common portion as discussed below.

The processor 112 may also provide control instructions to various components of the system 100. For example, the processor 112 controls the beamformer 104 to generate acoustic waveforms and scan formats and/or controls generating of a three-dimensional representation by the three-dimensional image processor 114. Alternatively, a separate processor provides control of the system 100.

The processor 112 or another processor may also coordinate user input. The user designates a region of interest on a displayed ultrasound image. For example, the region of interest corresponds to pixels associated with the enclosed structure for determination of a center axis or for dividing the common portion of a bifurcation. Alternatively, the region of interest is identified by the system 100 by applying one or more thresholds to the Doppler estimates or B-mode information. The identified regions, regardless of the process of identification, are stored in a memory of the processor 112, another processor or a memory separate from the processor 112. Alternatively, the user configures the system 100 to scan only the region of interest.

The processor 112 interacts with the three-dimensional image processor 114 to generate a three-dimensional representation of the vessel region of interest. The three-dimensional image processor 114 comprises a remote computer. For example, 3D image processor 114 comprises a remote workstation, such as the AEGIS® workstation of Acuson Corporation, or a remote personal computer, such as a Perspective® personal computer. Alternatively, an on-board computer is used, such as the processor 112 or another processor. For example, see U.S. Pat. No. 6,159,150, the disclosure of which is incorporated herein by reference.

For 3D imaging, a plurality of scans of the vessel are performed. The representation is rendered from data from different scan planes by the three-dimensional image processor 114. The data used comprises data output by the signal processor 106 or the scan converter 108, including Doppler velocity, Doppler energy, Doppler variance, B-mode and combinations thereof.

In one embodiment, the three-dimensional image processor 114 and the system 100 comprise the system described in U.S. Pat. No. 5,928,151, the disclosure of which is incorporated herein by reference. The system 100 operates as described in the above referenced '151 patent for rendering an image using data corresponding to harmonic or fundamental frequencies.

To render a three-dimensional representation, the scan planes for the data are aligned. Many approaches can be taken in aligning the image data frames to provide the desired three-dimensional reconstruction of the data. For example, mechanical or electrical systems determine a position of the transducer 102 relative to the patient for each scan plane (e.g. absolute position sensors as represented by optional sensor 103). This positioning device may be a magnetic sensor, such as those available from Ascension Technology, Burlington, Vt. Alternatively, the position of the scan planes may be assumed, entered manually or determined electronically from a 2D or 1.5D transducer array. In another alternative, the data may be used to determine the position of the scan plane, such as described in U.S. Pat. No. 6,014,473.

For reconstruction, the 3D image processor 114 uses the data frames and the position information to generate information for the three dimensional representation of a volume. Information from the two-dimensional image data frames is converted to a 3D grid, such as a regularly (equal) spaced volume grid. Successive image data frames are inserted into their appropriate XYZ locations of the 3D volume as a function of the positional information.

Once all frames have been inserted, intermediate points are calculated using three-dimensional interpolation techniques relying on the eight or other number of closest known data points. For example, data samples in the 3D grid are linearly interpolated from neighboring data samples, such as 4 or 8 samples. Other interpolation techniques may be used, such as spline fitting.

Instead of scan planes, spaced line data, such as associated with an ultrasound scan line, is used to interpolate to the 3D grid. These data samples are not yet interpolated to the arbitrary two-dimensional planes by scan conversion. Other approaches to 3D reconstruction may be used, such as a nearest neighbor search.

The 3D image processor 114 uses software to construct the 3D representation based on the input information discussed above. Various commercially available software and fixtures are available for 3D reconstruction. Alternatively, the software for reconstruction of the 3D representation is written specifically for the system 100 described above. The representation is displayed on the display 110.

Various visualization software, such as Fortner Research LLC's T3D, and techniques may be used to present the 3D image or reconstruction on the two-dimensional display. Cross sections can be taken in various planes, including a wide variety of planes selected by the user or the system 100 that do not correspond to the scan planes of the image data. The selected planes are interpolated from the 3D grid data samples. For 3D imaging, the 3D representation on the display 38 may be rotated, zoomed and viewed in perspective as is well known in the art.

Various techniques for 3D imaging are possible, such as surface renderings and volume rendering displays. Volume rendering techniques comprise alpha bending, maximum intensity projection or minimum intensity projection. As an alternative to the surface rendering discussed above, the polygon mesh is derived by applying border detection to each image plane (two-dimensional representation). A polygon mesh is formed by logically linking the detected borders.

The processor 112, the three-dimensional processor 114, the signal processor 106 or another processor automatically analyze the ultrasound data to locate the center axis and/or to divide the common portion of the bifurcation. Using a memory associated with the processor, such as a hard drive, RAM or other memory, the ultrasound data is stored. Alternatively, a separate memory structure that is independent of the processors is used. The stored data is used to locate the center axis or to determine a division of the common portion of the bifurcation.

II. Automated Structure Analysis

The system 100 automatically locates the center axis of a vessel. The user may indicate a region of interest for this analysis. In response to the user information and ultrasound data, the system 100 automatically determines the center axis.

Figure 2:
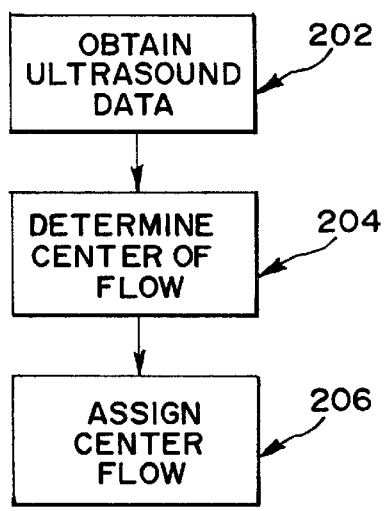
FIG. 2 is a flow chart representing one embodiment for automatically determining a medial axis of a vessel.

FIG. 2 shows a flow chart of one embodiment for automated structure analysis. In act 202, ultrasound data is obtained. A center of flow for a vessel is determined from the ultrasound data in act 204. In act 206, the center of flow is assigned as the center or medial axis of the vessel.

For act 202, the ultrasound data is obtained for a two or three-dimensional region. The ultrasound data obtained is in one of various formats. For example, polar or Cartesian coordinate data is obtained. The ultrasound data corresponds to one or more different scan planes or regions of the target. The regions overlap or are independent of each other. The regions correspond to a scanned area or a non-scanned area. For a non-scanned area, the ultrasound data is interpolated or extrapolated from other ultrasound data. For example, a data set representing a three-dimensional region of the target is obtained.

The ultrasound data is obtained using the system 100 or is imported from another system. For example, a linear transducer is slid along an elevational dimension to obtain the plurality of ultrasound data sets for imaging the carotid artery. The relative position of each scan or the transducer for each scan may also be obtained. As described above, Doppler estimates, such as Doppler energy, velocity or variance estimates, are obtained in response to each scan. Alternatively, B-mode or data that is a combination of Doppler estimates and/or B-mode data is obtained.

In one embodiment, one type of data is segmented from another type of data where a combination of types of data is obtained. For example, Doppler energy or velocity data is segmented from B-mode data, and the Doppler energy or velocity data is used to automatically analyze the vessel.

In one embodiment, the ultrasound data is processed to remove artifact, speckle or other noise related signals. For example, Doppler data is passed through a clutter filter to remove color flash artifacts. The processing is performed prior to or after obtaining the data for structure analysis.

The ultrasound data represents a vessel in the target. The processing of the ultrasound data to divide a common portion of the bifurcation (i.e., sculpting) and/or determine a center axis may be performed without regard to cyclical flow. However, the flow and associated Doppler information from a vessel may change as a function of time. For cyclical flow, such as in the carotid artery, the ultrasound data used for locating the center axis is phased to the cycle. For a cardiac cycle, an EKG trigger device triggers each scan so that data is acquired from a same phase of the cardiac cycle. As an alternative to the EKG device, data acquisition is phased in response to a cycle determined from Doppler data, such as phasing in response to a Doppler velocity cycle. For example, U.S. Pat. No. 6,190,321 discloses determining a phase of the cardiac cycle from color Doppler values extracted from a dual mode image.

Figure 3:
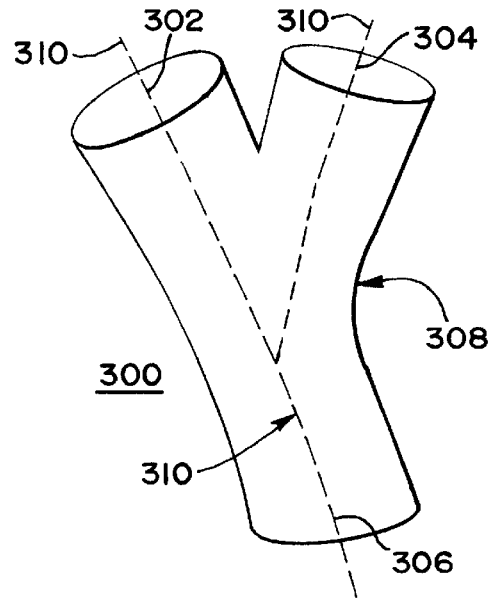
FIG. 3 is a graphical representation of one embodiment of a bifurcated vessel.

FIG. 3 shows one embodiment of a vessel 300 represented by the ultrasound data, such as a carotid artery. Other vessels with no bifurcations or with more bifurcations may be used.

The vessel 300 is identified from the ultrasound data. The end points 302, 304, 306 or section of the vessel for analysis are determined. For example, the end points 302, 304, 306 are determined as being at the edges of the three-dimensional region represented by the ultrasound data (i.e., the extent of the three-dimensional scan). As another example, the end points 302, 304, 306 of the vessel 300 for analysis are selected by the user. A three-dimensional representation is displayed, and the user indicates the end points 302, 304, 306. Ultrasound data associated with portions of the vessel 300 beyond the end points 302, 304, 306 is clipped or not used.

The end points 302, 304 and 306 are determined for each branch of the vessel 300. For example, the scans are associated with an approximately 4 cm section of the vessel (e.g. from the end point 306 to the bifurcation end points 302, 304 is about 4 cm). In this example, 2 cm of the vessel 300 for analysis is above a bifurcation 308 (e.g. carotid bulb) and 2 cm of the vessel 300 for analysis is below the bifurcation 308. Other spatial orientations, ranges and/or vessels may be used.

In one embodiment, ultrasound data associated with one or more vessels is automatically removed from the flow analysis. For example, scans of the carotid artery often include the jugular vein. To isolate the ultrasound data associated with the carotid artery from the ultrasound data associated with the jugular vein, the system 100 automatically analyzes the direction of flow or hemodynamics of the identified vessels. The direction of flow in the carotid artery is opposite to the direction of flow in the jugular vein. The sign of Doppler velocity estimates indicates the direction of flow. Based on user input (e.g. selection of a flow direction or vessel) or a known orientation of the transducer 102, the system 100 automatically identifies the carotid artery and jugular vein as a function of the sign. Alternatively, an assigned color for display based on Doppler velocity estimates is used to distinguish vessels (e.g. red for one direction and blue for the opposite direction). In yet another alternative, a structural feature is used to identify one vessel from another.

Other hemodynamic characteristics may be used to distinguish vessels, such as steady flow verses pulsitile flow, different flow cycles, speed of flow, volume of flow or area of flow. For example, ultrasound data associated with small vessel cross-sectional areas is removed. A threshold area is used to isolate larger vessels. Alternatively or additionally, the vessels are isolated as a function of relative size. Ultrasound data for all but the two largest vessel cross-sections is removed. Any of the various types of ultrasound data, such as Doppler velocity or energy data, may be used for determining hemodynamic characteristics.

In act 204, a center of flow within the vessel 300 between the end points 302, 304, 306 is determined. The system 100 determines the center of flow as a function of the ultrasound data. The ultrasound data representing flow in the vessel is used as weights associated with spatial locations within the vessel. The weights are equal to the ultrasound data or are determined as a function of the ultrasound data. Ultrasound data associated with regions external to the vessel are set to zero or not used.

Local first and second spatial derivatives along all directions of the weights or ultrasound data are determined for each spatial location. The first spatial derivate comprises the gradient. The gradient corresponds to the amplitude of change from one spatial location to another of the ultrasound data or weights. The local gradient is determined for one or more, such as three, dimensions. For example, the change in the ultrasound data values as a function of each of the x, y and z dimensions is determined. The change is determined for each set of two values representing adjacent spatial locations. To compute the spatial derivatives, the nearest neighbor or other groupings of data may be used.

In one embodiment, a magnitude of the local gradients is calculated. For each spatial location, the gradients for two or more dimensions are squared and summed. The square root of the result provides the magnitude of the gradient. Other functions may be used.

Where the magnitude of the local gradients is above a threshold value, a boundary of the vessel 300 is located. Alternatively, the boundary is determined as a function of the ultrasound data as discussed above.

The vessel is iteratively dilated. The boundary of the vessel 300 is reduced. The ultrasound data removed to dilate the boundary is determined as a function of the direction of the maximum gradient for each spatial location on the boundary. The direction corresponds to a vector angle determined from the two or three-dimensional gradient information.

The amount of reduction or dilation is a function of the magnitude of the local gradients in one embodiment. For example, the amount of reduction is substantially inversely proportional to the gradient magnitude. In an alternative embodiment, dilation is performed using the inverse diffusion equation, using the first and second spatial derivatives. In the inverse diffusion equation, time is set equal to the number of inverse diffusion iterations. In alternative embodiments, the ultrasound data, the weights or combinations thereof are used to determine the amount of reduction. Other functions may be used.

The center of flow is identified by this dilation. The boundary dilates to a three-dimensional curve representing the center of flow of the vessel 300. The curve is a function of the flow in the vessel 300. The center of flow is automatically provided for each branch of the vessel 300.

In act 206, the three-dimensional curve representing the center of flow is assigned as the center or medial axis 310 of the vessel 300. For turbulent flow, such as flow near a stenosis, the center axis is accurately determined as the center of flow.

In one embodiment, the center axis 310 is displayed on two or three dimensional representations. For example, a two dimensional image displayed includes a colored point or label indicating the center of flow. As another example, a three-dimensional representation of the vessel 300 includes a colored or opaque three-dimensional curve showing the center axis 310 of the vessel 300.

III. Automatic Division of Vessel Bifurcation

In one embodiment, the system 100 automatically divides a common portion of a vessel bifurcation between the branches from the bifurcation. At the bifurcation 308 of the embodiment of FIG. 3, two branches extend from a trunk of the vessel 300. For example, the vessel 300 comprises the carotid artery where an interior branch provides blood to the brain, and the exterior branch provides blood to the face.

Figure 4:
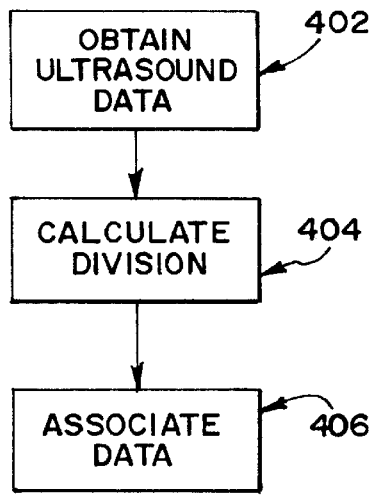
FIG. 4 is a flow chart representing one embodiment for automatically dividing a common portion of a bifurcated vessel.

FIG. 4 shows a flow chart of one embodiment for automated structure analysis. In act 402, ultrasound data representing a bifurcated vessel is obtained. The ultrasound data is obtained as discussed above. A division of flow or area between each branch in a common portion of the bifurcated vessel is calculated in act 404. In act 406, ultrasound data representing the common portion is associated with the branches as a function of the division.

Figure 5:
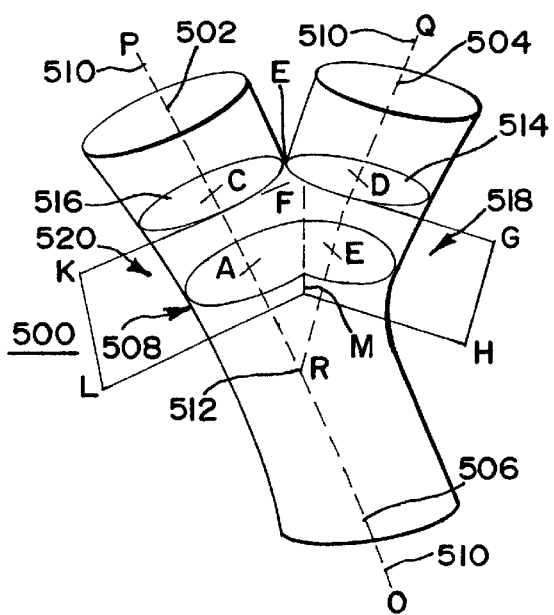
FIG. 5 is a graphical representation of one embodiment of the vessel of FIG. 3 with representative cross-sectional areas.

FIG. 5 shows one embodiment of a vessel 500 with a bifurcation 508. The center or medial axis 510 is determined as discussed above. Alternatively, the center axis 510 is determined by assuming a straight line between end points 502 or 504 and 506. In yet another alternative embodiment, the center axis 510 is determined as a function of a center of gravity calculation for each of a plurality of cross-sections of the vessel 500. Other techniques may be used, such as disclosed in (Ser. No. 09/607,556, filed Jun. 29, 2000) for a Medical Diagnostic Ultrasound System And Method For Flow Analysis, the disclosure of which is herein incorporated by reference. In other embodiments, the center axis 510 is not determined.

The bifurcation 508 comprises a common portion shared by the two branches. Additional branches may be provided. The common portion extends from a point R (the intersection of the center axis 510 from each branch) to the separation of the branches at points C and D. Point E corresponds to the exterior separation of the branches. Points C and D correspond to the center axis 510 location in respective planes perpendicular to the center axis 510 of each respective branch through the point E.

The flow within the common portion is attributable to flow in multiple branches. To assist medical diagnosis, the common portion or the flow corresponding to the common portion is divided between the branches.

For act 404, one or more techniques for dividing the common portion (e.g. bulb) of the vessel 300 are provided. In a first embodiment, a ratio calculated from ultrasound data determines the division of the common portion. In a second embodiment, the intersection of two or more planes determines the division of the common portion.

Due to the conservation of mass, the total volume flow entering the bifurcation is equal to the sum of the volume flow in each of the branches. In the first embodiment, a ratio of an integral of the ultrasound data for a cross-section of a first branch to an integral of the ultrasound data for a cross-section of a second branch is calculated. Preferably, the ultrasound data comprises Doppler energy or velocity data. Angle correction of the velocity data may be used.

The cross-sectional integral of each branch is determined after (e.g. distal) the separation at points E, C and D. Preferably, the cross-section is defined substantially close to the separation, such as cross-sections 514 and 516. For each cross-section 514, 516, a plane is defined that is perpendicular to the central axis 510 of the branch.

Ultrasound data or data derived from ultrasound data corresponding to spatial locations on each cross-sectional plane are summed. The ratio is calculated from the summations or integrals of ultrasound data. The ratio represents the amount of flow from the common area attributable to each branch. In alternative embodiments, the ratio is calculated as a function of areas of the cross-sections.

For act 406, a sub-set of ultrasound data representing the common portion is associated with each branch as a function of the ratio. For example, ⅜ of the flow from the common area is associated with the first branch and ⅝ of the flow is associated with another branch. For calculations using the amount of flow in the common portion for branch specific analysis, the ratio is applied to the total flow in the common portion. Alternatively, a cross-sectional area or other measurement of the common portion is associated with each branch as a function of the ratio. For example, constrictions are identified as a function of the cross-sectional area. Where one branch is being analyzed, the cross-sectional area for the common portion is multiplied by the ratio. The area or flow attributable to the branch not being analyzed does not alter the analysis of the cross-sectional area or flow along the branch being analyzed.

In one embodiment, Doppler velocity data is used for calculating the ratio. The Doppler velocity data is angle corrected to account for any difference between the angle of flow and the scanning angle. The difference is determined by measuring ultrasound data, by determining a position of the transducer relative to the center axis 510, or in response to user input indicating the direction of flow. In alternative embodiments, the velocity data is not angle corrected. In yet other alternative embodiments, other types of ultrasound data, such as Doppler energy data, is used.

In one embodiment, spatial locations in the common portion are assigned to each branch as a function of the ratio. Spatial locations within a threshold distance of the center axis 510 of each branch are assigned to the corresponding branch. For spatial locations equally distant from the center axis 510 of each branch, the locations are assigned so that the total number of locations assigned to each branch have a ratio equal to the ratio calculated as discussed above.

In the second embodiment for segmenting the common portion of the vessel 500, an intersection of two planes divides the common portion for act 404. For a location along the center axes 510 of the branches within the common portion, planes 518, 520 perpendicular to the center axes 510 are determined. The location for each center axis 510 is equally spaced from the point R. In alternative embodiments, the spacing along each center axis is determined by an equal number of spatial displacements given the distance from point R to points C and D. In alternative embodiments, surfaces other than planes may be used, such as curved surfaces normal to stream lines or associated with particle fronts (blood or contrast agent) flowing through the bifurcation.

The planes 518 and 520 intersect along a line through the common portions, such as along line MF. The intersection MF divides the common portion. This process is repeated for a plurality of locations spaced along the center axes 510 of the common portion. For example, the points A and B are stepped substantially equally or as a ratio of distances RC/RD along RC and RD. A plurality of intersections are determined. First, the intersection is determined adjacent to point R. A certain number of steps later, the intersection is determined adjacent to points C and D (i.e. point E).

For act 406, ultrasound data associated with spatial locations or the area on each side of the intersection is associated with the appropriate branch. The appropriate branch corresponds to the branch with the center axis perpendicular to the plane 518, 520 defining the intersection. The cross-sectional area or the ultrasound data is segmented between the two branches as a function of the intersection. As discussed above, the segmented area or ultrasound data allows for more accurate medical diagnosis.

As used in this application, the term "vessel" includes any enclosed region or zone in a body that permits fluid flow therein.

While the invention has been described above by reference to various embodiments, it will be understood that many changes and modifications can be made without departing from the scope of the invention. For example, the user may adjust or provide input during one or more of the various automatic acts described above. The ultrasound data used for any of the acts described herein may comprise Doppler energy, velocity, variance associated with fluid or tissue motion.

It is therefore intended that the foregoing detailed description be understood as an illustration of the presently preferred embodiments of the invention, and not as a definition of the invention. It is only the following claims, including all equivalents, that are intended to define the scope of this invention.

What is claimed is:

1. A medical diagnostic ultrasound method for automatically selecting a common portion of a vessel bifurcation attributable to a first branch with an ultrasound system, the method comprising the acts of:
   (a) obtaining ultrasound data representing the common portion of the vessel bifurcation;
   (b) calculating a division of the common portion with a processor; and
   (c) automatically associating a first sub-set of the ultrasound data with the first branch as a function of the division.

2. The method of claim 1 wherein (b) comprises calculating a ratio corresponding to the first branch and a second branch of the vessel bifurcation.

3. The method of claim 2 wherein the ultrasound data comprises flow data and (b) comprises calculating the ratio of an integral of flow data of a cross-section of the first branch to an integral of flow data of a cross-section of the second branch.

4. The method of claim 3 wherein (a) comprises obtaining energy ultrasound data.

5. The method of claim 3 wherein (a) comprises obtaining velocity ultrasound data.

6. The method of claim 1 wherein (a) comprises obtaining ultrasound data representing a cross-sectional area of the vessel bifurcation.

7. The method of claim 6 wherein (a) comprises obtaining ultrasound data representing a plurality of cross-sectional areas of the vessel bifurcation and (b) and (c) are performed for the plurality of cross-sectional areas.

8. The method of claim 1 further comprising:
   (d) determining a cross-sectional area corresponding to the first sub-set of the ultrasound data.

9. The method of claim 1 wherein (b) comprises:
   (b1) determining a first three-dimensional surface perpendicular to a first center axis of the first branch in the common portion;
   (b2) determining a second three-dimensional surface perpendicular to a second center axis of a second branch in the common portion; and
   (b3) determining an intersection of the first three-dimensional surface with the second three-dimensional surface; and
   wherein (c) comprises associating data representing locations in the first three-dimensional surface on a first side of the intersection as the first sub-set of ultrasound data.

10. The method of claim 9 further comprising:
    (d) associating data representing locations in the second three-dimensional surface on a second side of the intersection as a second sub-set of ultrasound data, the second sub-set free of ultrasound data in the first sub-set.

11. The method of claim 1 further comprising:
    (d) determining first and second center axes of the first branch and a second branch, respectively, of the vessel.

12. The method of claim 11 wherein (d) comprises determining the first and second center axes as a function of a center of flow.

13. The method of claim 11 wherein (d) comprises determining the first and second center axes as a function of local gradients of the ultrasound data.

14. The method of claim 11 wherein (d) comprises iteratively reducing a boundary of the vessel as a function of a gradient.

15. A medical diagnostic ultrasound system for automatically selecting a common portion of a vessel bifurcation attributable to a first branch, the system comprising:
    a memory for storing ultrasound data representing the common portion of the vessel bifurcation; and
    a processor operable to calculate a division of the common portion and automatically associate a first sub-set of the ultrasound data with the first branch as a function of the division.

16. The system of claim 15 wherein the ultrasound data comprises flow data and the processor is operable to calculate a ratio of an integral of flow data of a cross-section of the first branch to an integral of flow data of a cross-section of a second branch.

17. The system of claim 15 wherein the memory stores ultrasound data representing a cross-sectional area of the vessel bifurcation.

18. The system of claim 17 wherein the memory stores ultrasound data representing a plurality of cross-sectional areas of the vessel bifurcation and the processor calculates the division and performs the association for each of the plurality of cross-sectional areas.

19. The system of claim 15 wherein the processor determines a cross-sectional area corresponding to the first sub-set of the ultrasound data.

20. The system of claim 15 wherein the processor determines a first three-dimensional surface perpendicular to a first center axis of the first branch in the common portion, determines a second three-dimensional surface perpendicular to a second center axis of a second branch in the common portion, and determines an intersection of the first three-dimensional surface with the second three-dimensional surface; and
    wherein the processor associates data representing locations in the first three-dimensional surface on a first side of the intersection as the first sub-set of ultrasound data.

21. The system of claim 15 wherein the processor is further operable to determine first and second center axes of the first branch and a second branch, respectively, of the vessel as a function of a center of flow.

22. A medical diagnostic ultrasound method for determining a center axis of a vessel, the method comprising the acts of:
    (a) obtaining ultrasound data representing flow in the vessel;
    (b) determining a center of flow as a function of the ultrasound data with a processor; and
    (c) assigning the center of flow as the center axis.

23. The method of claim 22 further comprising:
    (d) calculating gradients as a function of the ultrasound data; and
    wherein (b) comprises determining the center of flow as a function of the gradients.

24. The method of claim 23 wherein (d) comprises calculating gradients in at least two dimensions for a plurality of spatial locations and further comprising:
    (e) calculating a magnitude of the gradients as a function of at least two dimensions for each of the plurality of spatial locations; and wherein (b) comprises determining the center of flow as a function of the magnitude.

25. The method of claim 22 further comprising:
(d) iteratively dilating a boundary of the vessel by an amount that is a function of the ultrasound data; and
wherein (b) comprises the boundary upon reduction to a line.

26. The method of claim 22 further comprising:
(d) reducing a boundary of the vessel by an amount that is a function of gradients of the ultrasound data; and
wherein (b) comprises the boundary upon reduction to a line.

27. The method of claim 22 wherein (a) comprises obtaining ultrasound data representing flow in the vessel in three-dimensions.

28. The method of claim 22 further comprising:
(d) determining a cross-sectional area perpendicular to the center axis.

29. The method of claim 22 wherein the vessel comprises a bifurcated vessel;
further comprising:
(d) assigning a sub-set of the ultrasound data associated with a portion of a common area; and
(e) determining the portion in response to the center axis.

30. A medical diagnostic ultrasound system for determining a center axis of a vessel, the system comprising:

a memory for storing ultrasound data representing flow in the vessel; and a processor for determining a center of flow as a function of the ultrasound data with a processor and for assigning the center of flow as the center axis.

31. The system of claim 30 wherein the processor calculates gradients in at least two dimensions for a plurality of spatial locations; and further calculates a magnitude of the gradients as a function of at least two dimensions for each of the plurality of spatial locations; and reduces a boundary of the vessel by an amount that is a function of the magnitude of the ultrasound data; and wherein center of flow comprises the boundary upon reduction to a line.

32. The method of claim 1 wherein (b) and (c) comprise sculpting the vessel bifurcation.

33. The method of claim 11 wherein (d) comprises determining the first and second center axes as a function of ultrasound data.

34. The method of claim 11 wherein (d) comprises applying an inverse diffusion equation.

35. The method of claim 22 wherein (b) comprises applying an inverse diffusion equation.

* * * * *